United States Patent [19]

Clements-Jewery et al.

[11] Patent Number: 4,847,268
[45] Date of Patent: Jul. 11, 1989

[54] 8-PHENYLTHIO-TETRAHYDROQUINO-LINES AND ANTI-ALLERGIC USE THEREOF

[75] Inventors: Stephen Clements-Jewery; Peter D. Kennewell, both of Wilts; Robert Westwood, Oxon, all of Great Britain

[73] Assignee: Roussel Uclaf, Paris, France

[21] Appl. No.: 62,883

[22] Filed: Jun. 16, 1987

[30] Foreign Application Priority Data

Jun. 25, 1986 [GB] United Kingdom ............... 86-15563

[51] Int. Cl.$^4$ .................... C07D 215/36; A61K 31/47
[52] U.S. Cl. .................................... 514/311; 546/178; 546/179
[58] Field of Search ................. 546/178, 179; 514/311

[56] References Cited

U.S. PATENT DOCUMENTS 3,509,159  4/1970  Kealey ................................ 546/179

Primary Examiner—David B. Springer
Attorney, Agent, or Firm—Bierman and Muserlian

[57] ABSTRACT

A compound selected from the group consisting of 8-phenylthio-tetrahydroquinolines of the formula

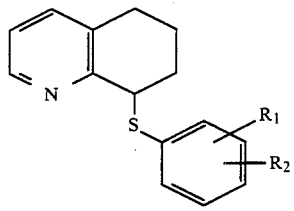

I wherein $R_1$ and $R_2$ are individually selected from the group consisting of hydrogen, halogen, alkyl of 1 to 6 carbon atoms optionally substituted with hydroxy, alkoxy of 1 to 6 carbon atoms, alkanoyloxy of 1 to 6 carbon atoms, alkoxycarbonyl of 2 to 6 carbon atoms, —OH, —NO$_2$, —NH$_2$, —COOH, —CN and aminosulfonyl or when $R_1$ and $R_2$ are on adjacent carbon atoms form with the said carbon atoms phenyl and their non-toxic, pharmaceutically acceptable acid addition salts having anti-allergic activity.

21 Claims, No Drawings

8-PHENYLTHIO-TETRAHYDROQUINOLINES AND ANTI-ALLERGIC USE THEREOF

OBJECTS OF THE INVENTION

It is an object of the invention to provide the novel compounds of formula I and their non-toxic, pharmaceutically acceptable acid addition salts and their preparation.

It is another object of the invention to provide novel anti-allergic compositions and a novel method of treating allergic conditions in warm-blooded animals.

These and other objects and advantages of the invention will become obvious from the following detailed description.

THE INVENTION

The novel compounds of the invention are selected from the group consisting of 8-phenylthio-tetrahydroquinolines of the formula

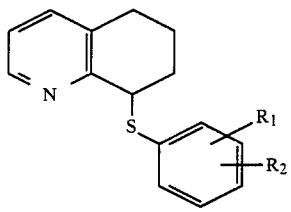

I wherein $R_1$ and $R_2$ are individually selected from the group consisting of hydrogen, halogen, alkyl of 1 to 6 carbon atoms optionally substituted with hydroxy, alkoxy of 1 to 6 carbon atoms, alkanoyloxy of 1 to 6 carbon atoms, alkoxycarbonyl of 2 to 6 carbon atoms, —OH, —$NO_2$, —$NH_2$, —COOH, —CN and aminosulfonyl or when $R_1$ and $R_2$ are on adjacent carbon atoms form with the said carbon atoms phenyl and their non-toxic, pharmaceutically acceptable acid addition salts.

Examples of preferred halogens are chlorine and bromine and examples of alkyl and alkoxy of 1 to 6 carbon atoms are methyl, ethyl, n-propyl, isopropyl and linear or branched butyl, pentyl and hexyl, methoxy, ethoxy, n-propoxy, isopropoxy and linear and branched butoxy, pentyloxy and hexyloxy. Examples of hydroxyl alkyl or 1 to 6 carbon atoms are hydroxymethyl, 2-hydroxyethyl, 3-hydroxypropyl, 4-hydroxybutyl, 5-hydroxypentyl, 6-hydroxyhexyl and 1-hydroxyhexyl.

Examples of alkanoyloxy of 1 to 6 carbon atoms are formyloxy, acetoxy, propionyloxy and linear and branched butyryloxy, pentanoyloxy and hexanoyloxy. Examples of alkoxycarbonyl of 2 to 6 carbon atoms are methoxycarbonyl, ethoxycarbonyl, n-propoxycarbonyl, isopropoxycarbonyl and linear and branched butoxycarbonyl and pentyloxycarbonyl.

Examples of suitable acids for the formation of the non-toxic, pharmaceutically acceptable acid addition salts are inorganic acids such as hydrochloric acid, hydroiodic acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid and aspartic acid, arylcarboxylic acids such as benzoic acid, alkane sulfonic acids such as methanesulfonic acid and arylsulfonic acid such as benzenesulfonic acid.

Among the preferred compounds of formula I are those wherein $R_1$ and $R_2$ are individually selected from the group consisting of hydrogen, chlorine, alkyl and hydroxyalkyl of 1 to 6 carbon atoms, alkoxy and alkanoyloxy of 1 to 6 carbon atoms, alkoxycarbonyl of 2 to 6 carbon atoms, —OH and —$NO_2$ or taken together with their adjacent carbon atoms to which they are attached form phenyl. Particularly preferred are the compounds of formula I wherein $R_1$ is hydrogen and $R_2$ is hydrogen, chlorine, methyl, n-butyl, methoxy, n-butoxyl, 1-hydroxyhexyl, —OH, —$NO_2$ or acetoxy or $R_1$ and $R_2$ together with the adjacent carbon atoms to which they are attached form phenyl and their non-toxic, pharmaceutically acceptable acid addition salts.

Specific preferred compounds of the invention are 8-(4-n-butylphenylthio)-5,6,7,8-tetrahydroquinoline, 8-(2-naphthylthio)-5,6,7,8-tetrahydroquinoline and 8-(4-methylphenylthio)-5,6,7,8-tetrahydroquinoline and their hydrochloride salts and 8-(1-naphthylthio)-5,6,7,8,-tetrahydroquinoline.

A novel process for the preparation of the compounds of formula I (process A) comprises reacting a salt of a compound of the formula

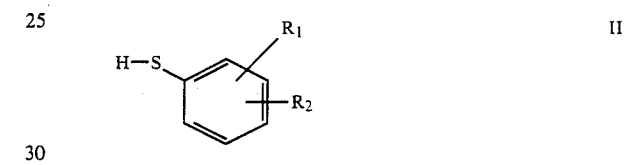

II wherein $R_1$ and $R_2$ are defined as above with a compound of the formula

III wherein $R_3$ is halogen such as chlorine, bromine or iodine to obtain the corresponding compound of formula I which may be salified, if desired.

The reaction is preferably effected in an organic solvent such as ether, tetrahydrofuran or dimethylformamide and the salt is formed by reacting a compound of formula II with an anion generating reagent such as an alkali metal hydride or alkali metal carbonate such as sodium hydride or potassium carbonate.

An alternative process of the invention for the preparation of the compounds of formula I wherein at least one of $R_1$ and $R_2$ are alkoxy or alkanoyloxy of 1 to 6 carbon atoms (process B) comprises reacting a salt of a compound of the formula

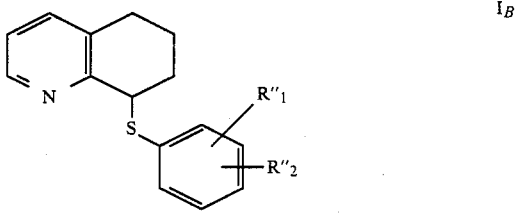

$I_B$ wherein $R_1''$ and $R_2''$ have the definition of $R_1$ and $R_2$ with the proviso that at least one is —OH with a compound of the formula

R—X    IV wherein R is alkyl or alkanoyl of 1 to 6 carbon atoms and X is a halogen such as chlorine, bromine or iodine or alkanoyloxy of 1 to 6 carbon atoms such as acetoxy to obtain a compound of the formula

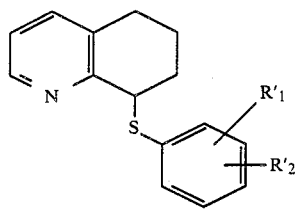

$I_A$ wherein $R_1'$ and $R_2'$ have the definition of $R_1$ and $R_2$ with the proviso that at least one of $R_1'$ and $R_2'$ is alkoxy or alkanoyloxy of 1 to 6 carbon atoms and optionally salifying the latter.

The reaction is preferably effected in an organic solvent such as tetrahydrofuran and dimethylformamide; when X is an alkanoyloxy of 1 to 6 carbon atoms in the compound of formula IV, the resulting anhydride is used to serve as both reagent and solvent so no other solvent is needed. The salt of the compound of formula $I_B$ may be prepared as before with an alkali metal hydride such as sodium hydride, for example.

The compounds of formula I wherein at least one of $R_1$ and $R_2$ represents an alkoxycarbonyl group of 2 to 6 carbon atoms may be prepared by reacting a compound of the formula

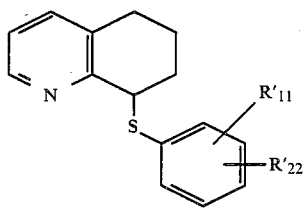

$I_D$ wherein $R_{11}'$ and $R_{22}'$ have the definition of $R_1$ and $R_2$ with the proviso that at least one of $R_{11}'$ and $R_{22}'$ is carboxy or a reactive derivative thereof with an alcohol of the formula

R'—OH    V wherein R' is alkyl of 1 to 5 carbon atoms, preferably in the presence of an inorganic acid such as hydrochloric acid to form the ester of the formula

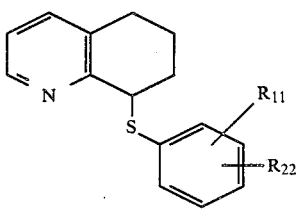

$I_C$ wherein $R_{11}$ and $R_{22}$ have the definition of $R_1$ and $R_2$ but at least one is alkoxycarbonyl of 2 to 6 carbon atoms.

The reaction of the alcohol of formula V may be effected in an excess of the alcohol which acts as the solvent and the reaction is preferably effected at elevated temperatures such as reflux. The compound of formula $I_D$ may be made by process A or B described above.

A process for the preparation of compounds of the formula

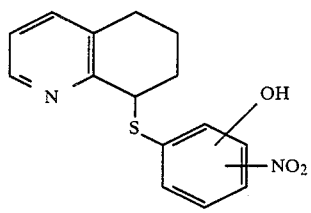

$I_E$ comprises nitrating a compound of the formula

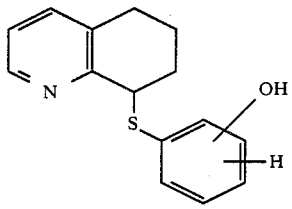

$I_F$ and the subsequent compound of formula $I_E$ may be salified. The nitration can be effected by known procedures such as reaction with a mixture of sodium nitrate and lanthanum nitrate in the presence of an inorganic acid such as hydrochloric acid in an organic solvent such as ether at a low temperature of 0° to 5° C., for example.

The compound of formula $I_F$ may be prepared by process A and the compound of formula $I_E$ may be converted into other compounds of formula I by process B.

The compounds of formula I may be converted into their acid addition salts by reaction with an approximately stoichiometric amounts of the acid and the compound of formula I with or without isolation thereof in a suitable solvent.

The novel anti-allergic compositions of the invention are comprised of an anti-allergically effective amount of at least one compound of formula I and their non-toxic, pharmaceutically acceptable acid addition salts and an inert pharmaceutical carrier or excipient. The compositions may be in the form of tablets, dragees, capsules, powders, suppositories, aerosols, creams, ointments and injectable solutions or suspensions.

Examples of suitable excipients, are talc, gum arabic, lactose, starch, magnesium stearate, cocoa butter, aqueous and nonaqueous vehicles, animal and vegetable fats, paraffins, glycols, diverse wetting agents, dispersants and emulsifiers and preservatives.

The compositions have a remarkable ability to inhibit 5-lipoxygenase and to bind leukotriene $D_4$ to its receptors and are useful for the treatment of allergic conditions such as asthmatic conditions and bronchitis of allergic origin.

The novel method of the invention for treating allergic conditions in warm-blooded animals, including humans, comprises administering to warm-blooded animals an anti-allergically effective amount of at least one compound of formula I and their non-toxic, pharmaceutically acceptable acid addition salts. The compounds may be administered orally, rectally, topically or parenterally and the usual daily dosage is 0.0015 to 2.8 mg/kg depending on the condition treated, method of administration and the compound used.

In the following examples there are described several preferred embodiments to illustrate the invention. However, it is to be understood that the invention is not intended to be limited to the specific embodiments.

EXAMPLE 1

8-(4-chlorophenylthio)-5,6,7,8-tetrahydroquinoline hydrochloride 1.65 g (55 mmol) of sodium hydride (80%) were added in portions to a stirred solution of 3.62 g (25 mmol) of 4-chloro-benzenethiol in 36 ml of dry dimethylformamide under nitrogen and cooled in ice. After evolution of hydrogen had ceased, 4.80 g (20 mmol) of 8-chloro-5,6,7,8-tetrahydroquinoline hydrochloride were added and the mixture was stirred at room temperature overnight. The solvent was removed under reduced pressure in a stream of nitrogen below 50° C. and 4N aqueous sodium hydroxide was added. The mixture was extracted with ethyl acetate and the extracts were washed with ice-cold aqueous sodium hydroxide and then with aqueous saturated sodium chloride, dried over $MgSO_4$ and evaporated to dryness under reduced pressure. A solution of the resulting oil in ether was treated with ethereal hydrogen chloride to precipitate 5.13 g (82%) of 8-(4-chlorophenylthio)-5,6,7,8-tetrahydroquinoline hydrochloride as colorless crystals (from ethanol-ether).

EXAMPLE 2

4-(5,6,7,8-tetrahydroquinoline-8-ylthio)-benzonitrile

A mixture of 4.08 g (20 mmol) of 8-chloro-5,6,7,8-tetrahydroquinoline hydrochloride, 3.38 g (25 mmol) of 4-mercaptobenzonitrile and 6.91 g (50 mmol) of potassium carbonate in 34 ml of dimethylformamide was stirred under nitrogen at room temperature overnight. The mixture was poured into aqueous saturated sodium chloride and was extracted with ethyl acetate. The extract was washed with ice-cold aqueous 2N sodium hydroxide and water, dried over $MgSO_4$ and evaporated under reduced pressure to obtain 4.72 g (89%) of 4-(5,6,7,8-tetrahydroquinoline-8-ylthio)-benzonitrile as colorless crystals (from methanoldichloromethane).

EXAMPLES 3 TO 16

Using the procedure of Example 1, the compounds of Examples 3 to 16 were prepared.
EXAMPLE 3: 8-(3-chlorophenylthio)-5,6,7,8-tetrahydroquinoline hydrochloride.
EXAMPLE 4: 8-(4-nitrophenylthio)-5,6,7,8-tetrahydroquinoline hydrochloride.
EXAMPLE 5: 8-(4-methylphenylthio)-5,6,7,8-tetrahydroquinoline hydrochloride.
EXAMPLE 6: 8-(1-naphthylthio)-5,6,7,8-tetrahydroquinoline.
EXAMPLE 7: 8-(4-aminophenylthio)-5,6,7,8-tetrahydroquinoline.
EXAMPLE 8: 8-(4-hydroxyphenylthio)-5,6,7,8-tetrahydroquinoline.
EXAMPLE 9: 8-(2-naphthylthio)-5,6,7,8-tetrahydroquinoline hydrochloride.
EXAMPLE 10: 8-(4-n-butylphenylthio)-5,6,7,8-tetrahydroquinoline hydrochloride.
EXAMPLE 11: 8[3-(1-hydroxyhexyl)-phenylthio]-5,6,7,8-tetrahydroquinoline.
EXAMPLE 12: 4-(5,6,7,8-tetrahydroquinoline-8-ylthio)-benzenesulfonamide.
EXAMPLE 13: 8-(phenylthio)-5,6,7,8-tetrahydroquinoline.
EXAMPLE 14: 8-(4-methoxyphenylthio)-5,6,7,8-tetrahydroquinoline hydrochloride.
EXAMPLE 15: 8-(4-ethylphenylthio)-5,6,7,8-tetrahydroquinoline hydrochloride.
EXAMPLE 16: 4-(5,6,7,8-tetrahydroquinoline-8-ylthio)-benzoic acid.

EXAMPLE 17

8-(4-n-Butoxyphenylthio)-5,6,7,8-tetrahydroquinoline hydrochloride 0.72 g (24 mmol) of sodium hydride were added to a solution of 5.15 g (20 mmol) of 8-(4-hydroxyphenylthio)-5,6,7,8-tetrahydroquinoline in 26 ml of dimethylformamide under nitrogen. When effervescence had ceased, 3.29 g (24 mmol) of n-bromobutane were added dropwise with ice-cooling. After stirring at room temperature overnight, the mixture was poured into ice-cold water and extracted with ether to obtain a brown oil. A solution of the oil in ether was treated with ethereal hydrogen chloride to precipitate 4.89 g (70%) of 8-(4-n-butoxyphhenylthio)-5,6,7,8-tetrahydroquinoline hydrochloride as pale yellow crystals (from ethanol-ether).

EXAMPLE 18

8-(4-ethoxyphenylthio)-5,6,7,8-tetrahydroquinoline hydrochloride

Using the procedure of Example 17, but using bromoethane in place of n-bromobutane 8-(4-ethoxyphenylthio)-5,6,7,8-tetrahydroquinoline hydrochloride was prepared.

EXAMPLE 19

8-(4-acetoxyphenylthio)-5,6,7,8-tetrahydroquinoline hydrochloride

A mixture of 4.0 g (15.6 mmol) of 8-(4-hydroxyphenylthio)-5,6,7,8-tetrahydroquinoline in 40 ml of acetic anhydride was heated under reflux for 2 hours. A reagent was then removed under reduced pressure and the residue was subjected to flash chromatography (Kieselgel 60; 5% ethyl acetate in dichloromethane). The thick yellow oil thus obtained was treated with ethereal hydrogen chloride to yield 3.4 g (49%) of 8-(4-acetoxyphenylthio)-5,6,7,8-tetrahydroquinoline hydrochloride.

EXAMPLE 20

Methyl 4-(5,6,7,8-tetrahydroquinoline-8-ylthio)-benzoate hydrochloride 4.24 g (15 mmol) of 4-(5,6,7,8-tetrahydroquinoline-8-ylthio)-benzoic acid prepared by a method analogous to Example 1 were stirred in 30 ml of refluxing methanol saturated with hydrogen chloride for 2 hours and the solvent was then removed under reduced pressure. The residue was dissolved in iced water, made alkaline with sodium carbonate and extracted with ether. The residue obtained upon evaporation of the solvent was treated with ethereal hydrogen chloride to yield 2.9 g (62%) of methyl 4-(5,6,7,8-tetrahydroquinoline-8-ylthio)-benzoate hydrochloride.

phenylthio)-5,6,7,8-tetrahydroquinoline as yellow crystals (from ethanol).

Yield, melting point and analytical data for the compounds of Examples 1 to 21 are given in Table I.

TABLE I

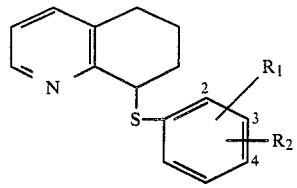

| Example | $R_1$ | $R_2$ | Yield % | MP (°C.) | Formula | Theory/Found C | H | N | S |
|---|---|---|---|---|---|---|---|---|---|
| 1 | H | 4-Cl | 82 | 130–52 | $C_{15}H_{15}Cl_2NS$* | 57.70 | 4.84 | 4.49 | |
| | | | | | | 57.57 | 4.90 | 4.49 | |
| 2 | H | 4-CN | 87 | 117–20 | $C_{16}H_{14}N_2S$ | 72.15 | 5.30 | 10.52 | |
| | | | | | | 72.24 | 5.35 | 10.52 | |
| 3 | 3-Cl | H | 79 | 148–60 | $C_{15}H_{15}Cl_2NS$* | 57.70 | 4.84 | 4.49 | |
| | | | | | | 57.91 | 4.87 | 4.57 | |
| 4 | H | 4-$NO_2$ | 80 | 154–60 | $C_{15}H_{15}ClN_2O_2S$* | 55.81 | 4.68 | 8.68 | |
| | | | | | | 55.59 | 4.71 | 8.68 | |
| 5 | H | 4-$CH_3$ | 75 | 157–71 | $C_{16}H_{18}ClNS$* | 65.85 | 6.22 | 4.80 | |
| | | | | | | 65.45 | 6.23 | 4.83 | |
| 6 | | 2,3-$C_4H_4$ | 63 | 96–7 | $C_{19}H_{17}NS$ | 78.31 | 5.88 | 4.81 | |
| | | | | | | 77.98 | 5.94 | 4.74 | |
| 7 | H | 4-$NH_2$ | 41 | 129–31 | $C_{15}H_{16}N_2S$ | 70.28 | 6.29 | 10.93 | |
| | | | | | | 70.13 | 6.30 | 10.87 | |
| 8 | H | 4-OH | 66 | 189–90 | $C_{15}H_{15}NOS$ | 70.01 | 5.88 | 5.44 | |
| | | | | | | 70.05 | 5.90 | 5.45 | |
| 9 | | 3,4-$C_4H_4$ | 84 | 151–160 | $C_{19}H_{18}ClNS$* | 69.60 | 5.53 | 4.27 | |
| | | | | | | 70.41 | 5.61 | 4.32 | |
| 10 | H | 4-n-butyl | 87 | 127–46 | $C_{19}H_{24}ClNS$* | 68.34 | 7.24 | 4.20 | |
| | | | | | | 68.31 | 7.29 | 4.19 | |
| 11 | 3-(1-hydroxyhexyl) | H | 82 | 54–63 | $C_{21}H_{27}NOS$ | 73.86 | 7.97 | 4.10 | 9.39 |
| | | | | | | 73.53 | 8.03 | 4.07 | 9.36 |
| 12 | H | 4-$SO_2NH_2$ | 29 | 184–7 | $C_{15}H_{16}N_2O_2S_2$ | 56.23 | 5.03 | 8.74 | |
| | | | | | | 56.19 | 5.04 | 8.76 | |
| 13 | H | H | 15 | (oil) | $C_{15}H_{15}NS$ | 74.64 | 6.28 | 5.80 | 13.28 |
| | | | | | | 74.44 | 6.37 | 5.69 | 13.10 |
| 14 | H | 4-methoxy | 64 | 127–42 | $C_{16}H_{18}ClNOS$*·¼$H_2O$ | 61.53 | 5.97 | 4.49 | |
| | | | | | | 61.57 | 5.84 | 4.49 | |
| 15 | H | 4-ethyl | 73 | 163–7 | $C_{17}H_{20}ClNS$* | 66.75 | 6.59 | 4.58 | |
| | | | | | | 66.54 | 6.70 | 4.40 | |
| 16 | H | 4-COOH | 45 | 199–204 | $C_{16}H_{15}NO_2S$ | 67.34 | 5.30 | 4.91 | |
| | | | | | | 67.14 | 5.32 | 4.82 | |
| 17 | H | 4-n-butoxy | 70 | 121–8 | $C_{19}H_{24}ClNOS$* | 65.22 | 6.91 | 4.00 | |
| | | | | | | 64.83 | 6.85 | 3.96 | |
| 18 | H | 4-OEt | 71 | 150–4 | $C_{17}H_{20}ClNOS$* | 63.44 | 6.26 | 4.35 | |
| | | | | | | 63.10 | 6.25 | 4.29 | |
| 19 | H | 4-OCOCH$_3$ | 49 | 98–102 | $C_{17}H_{18}ClNO_2S·H_2O$* | 57.90 | 5.70 | 3.96 | |
| | | | | | | 57.82 | 5.74 | 3.82 | |
| 20 | H | 4-COOCH$_3$ | 62 | 150–5 | $C_{17}H_{18}ClNO_2S$* | 60.79 | 5.40 | 4.17 | |
| | | | | | | 60.49 | 5.47 | 4.09 | |
| 21 | 3-$NO_2$ | 4-OH | 20 | 122–4 | $C_{15}H_{14}N_2O_3S$ | 59.58 | 4.72 | 9.27 | |
| | | | | | | 59.48 | 4.67 | 9.21 | |

*HCl salt

EXAMPLE 21

8-(4-hydroxy-3-nitrophenylthio)-5,6,7,8-tetrahydroquinoline 15.0 g (58 mmol) of 8-(4-hydroxyphenylthio)-5,6,7,8-tetrahydroquinoline in 90 ml of ether were added dropwise to a stirred solution of 4.96 g (58 mmol) of sodium nitrate and 0.25 g (58 mmol) of lanthanum nitrate in 60 ml of 5.5N hydrochloric acid at 0° to 5° C. in an icebath. Stirring was then continued under nitrogen for 24 hours, after which water was added and the mixture was extracted with chloroform. Removal of solvent left a yellow oil which was purified by flash chromatography (Kieselgel 60; 10% ethyl acetate in dichloromethane) to obtain 5.6 g (20%) of 8-(4-hydroxy-3-nitro-

EXAMPLE 22

Tablets were prepared containing 20 mg of the compound of Example 6 or 10 and sufficient excipient of lactose, starch, talc, magnesium stearate to form a final tablet weight of 100 mg.

EXAMPLE 23

A dosed aerosol was prepared delivering per dose: 2 mg of the compound of Example 9, 0.15 mg of emulsifier and 50 mg of propellant.

PHARMACOLOGICAL DATA

A. 5-LIPOX

Inhibition of the $Ca^{++}$ ionophore (A23187)-induced release of 5-lipoxygenase products (leukotriene $D_4$ and 5-HETE) from [$^{14}C$]-arachidonic acid pre-labelled rat peritoneal neutrophils. Assayed by a modification of the method reported by Ahnfelt-Ronne et al [Biochemical Pharmacology, Vol. 31, No. 16, pp. 2619–2624 (1982)]. The data presented are micromolar concentrations of test compound causing 50% inhibition of control response determined graphically from dose-response curves.

B. $LTD_4$ RECEPTOR

Inhibition of the specific binding of [$^3H$]-$LTD_4$ to a membrane preparation of guinea-pig lung tissue assayed by a modification of a method reported by Bruns et al [Life Sciences, Vol. 33, pp. 645–653 (1983)]. The data presented are micromolar concentrations of test compound causing 50% inhibition of specific binding determined graphically from dose-response curves. The results of these tests are given in Table II.

TABLE II

| Example | 5-LIPOX | $LTD_4$ receptor |
|---|---|---|
| 1 | 4.2 | 22.4 |
| 2 | 31 | |
| 4 | 12.6 | 26.3 |
| 5 | 3.0 | 23.4 |
| 6 | 1.7 | 52.5 |
| 7 | 25 | >100 |
| 8 | 14.1 | |
| 9 | 2.3 | |
| 10 | 1.9 | |
| 11 | 5.6 | |
| 12 | 26 | |
| 14 | 13.2 | 16.6 |
| 15 | 4.0 | |
| 16 | >100 | |
| 17 | 3.7 | |
| 18 | 11.2 | |
| 19 | 45 | |
| 20 | 18.6 | |
| 21 | 33 | |

Various modifications of the compounds and method of the invention may be made without departing from the spirit or scope thereof and it should be understood that the invention is intended to be limited only as defined in the appended claims.

What is claimed is:

1. A compound selected from the group consisting of 8-phenylthio-tetrahydroquinoline of the formula

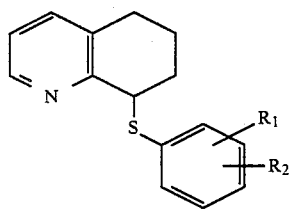

(I)

wherein $R_1$ and $R_2$ are individually selected from the group consisting of hydrogen, halogen, alkyl of 1 to 6 carbon atoms optionally substituted with hydroxy, alkoxy of 1 to 6 carbon atoms, alkanoyloxy of 1 to 6 carbon atoms, alkoxycarbonyl of 2 to 6 carbon atoms, —OH, —$NO_2$, —$NH_2$, —COOH, —CN and aminosulfonyl or when $R_1$ and $R_2$ are on adjacent carbon atoms form with the said carbon atoms

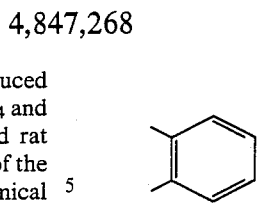

and their non-toxic, pharmaceutically acceptable acid addition salts.

2. A compound of claim 1 wherein $R_1$ and $R_2$ are individually selected from the group consisting of hydrogen, chlorine, alkyl and hydroxyalkyl of 1 to 6 carbon atoms, alkoxy and alkanoyloxy of 1 to 6 carbon atoms, alkoxycarbonyl of 2 to 6 carbon atoms, —OH and —$NO_2$ or taken together with the adjacent carbon atoms to which they are attached form

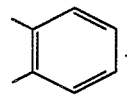

3. A compound of claim 1 wherein $R_1$ is hydrogen and $R_2$ is selected from the group consisting of hydrogen, chlorine, methyl, n-butyl, methoxy, n-butoxy, 1-hydroxyhexyl, —OH, acetoxy and —$NO_2$ or $R_1$ and $R_2$ are on adjacent carbon atoms with which they form

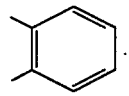

4. A compound of claim 1 selected from the group consisting of 8-(1-naphthylthio)-5,6,7,8-tetrahydroquinoline and its non-toxic, pharmaceutically acceptable acid addition salts.

5. A compound of claim 1 selected from the group consisting of 8-(2-naphthylthio)-5,6,7,8-tetrahydroquinoline and its hydrochloride salt.

6. A compound of claim 1 selected from the group consisting of 8-(4-n-butylphenylthio)-5,6,7,8-tetrahydroquinoline and its hydrochloride salt.

7. A compound of claim 1 selected from the group consisting of 8-(4-methylphenylthio)-5,6,7,8-tetrahydroquinoline and its hydrochloride salt.

8. An anti-allergic composition comprising an anti-allergically effective amount of a compound of claim 1 and an inert pharmaceutical carrier.

9. A composition of claim 8 wherein in the active compound $R_1$ and $R_2$ are individually selected from the group consisting of hydrogen, chlorine, alkyl and hydroxyalkyl of 1 to 6 carbon atoms, alkoxy and alkanoyloxy of 1 to 6 carbon atoms, alkoxycarbonyl of 2 to 6 carbon atoms, —OH and —$NO_2$ or taken together with the adjacent carbon atoms to which they are attached form

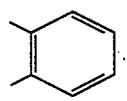

10. A composition of claim 8 wherein in the active compound $R_1$ is hydrogen and $R_2$ is selected from the group consisting of hydrogen, chlorine, methyl, n-butyl, methoxy, n-butoxy, 1-hydroxyhexyl, —OH, acetoxy and —NO$_2$ or R$_1$ and R$_2$ are on adjacent carbon atoms with which they form

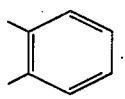

11. A composition of claim 8 wherein the active compound is selected from the group consisting of 8-(1-naphthylthio)-5,6,7,8-tetrahydroquinoline and its nontoxic, pharmaceutically acceptable acid addition salts.

12. A composition of claim 8 wherein the active compound is selected from the group consisting of 8-(2-naphthylthio)-5,6,7,8-tetrahydroquinoline and its hydrochloride salt.

13. A composition of claim 8 wherein the active compound is selected from the group consisting of 8-(4-n-butylphenylthio)-5,6,7,8-tetrahydroquinoline and its hydrochloride salt.

14. A composition of claim 8 wherein the active compound is selected from the group consisting of 8-(4-methylphenylthio)-5,6,7,8-tetrahydroquinoline and its hydrochloride salt.

15. A method of treating allergic conditions in warm-blooded animals comprising administering to warm-blooded animals an anti-allergically effective amount of a compound of claim 1.

16. A method of claim 15 wherein in the active compound R$_1$ and R$_2$ are individually selected from the group consisting of hydrogen, chlorine, alkyl and hydroxyalkyl of 1 to 6 carbon atoms, alkoxy and alkanoyloxy of 1 to 6 carbon atoms, alkoxycarbonyl of 2 to 6 carbon atoms, —OH and —NO$_2$ or taken together with the adjacent carbon atoms to which they are attached form

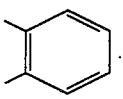

17. A method of claim 15 wherein in the active compound R$_1$ is hydrogen and R$_2$ is selected from the group consisting of hydrogen, chlorine, methyl, n-butyl, methoxy, n-butoxy, 1-hydroxyhexyl, —OH, acetoxy and —NO$_2$ or R$_1$ and R$_2$ are on adjacent carbon atoms with which they form

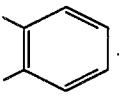

18. A method of claim 15 wherein the active compound is selected from the group consisting of 8-(1-naphthylthio)-5,6,7,8-tetrahydroquinoline and its nontoxic, pharmaceutically acceptable acid addition salts.

19. A method of claim 15 wherein the active compound is selected from the group consisting of 8-(2-naphthylthio)-5,6,7,8-tetrahydroquinoline and hydrochloride salt.

20. A method of claim 15 wherein the active compound is selected from the group consisting of 8-(4-n-butylphenylthio)-5,6,7,8-tetrahydroquinoline and its hydrochloride salt.

21. A method of claim 15 wherein the active compound is selected from the group consisting of 8-(4-methylphenylthio)-5,6,7,8-tetrahydroquinoline and its hydrochloride salt.

* * * * *